United States Patent [19]
Bean

[11] Patent Number: 5,964,004
[45] Date of Patent: Oct. 12, 1999

[54] DEVICE FOR CLEANING MEDICAL ENDOSCOPIC TUBES

[76] Inventor: Douglas Colin Bean, 84 Lewis Road, Wantirna South, Victoria 3152, Australia

[21] Appl. No.: 08/936,459

[22] Filed: Sep. 24, 1997

[30] Foreign Application Priority Data

Sep. 24, 1996 [AU] Australia ............................... 65818/96
Apr. 11, 1997 [AU] Australia ............................... PO 6153

[51] Int. Cl.⁶ .................................................. B08B 9/00
[52] U.S. Cl. ...................................... 15/104.16; 15/104.05
[58] Field of Search ......................... 15/104.05, 104.062, 15/104.061, 104.16, 236.05, 236.07, 211, 104.2, 236.06

[56] References Cited

U.S. PATENT DOCUMENTS

| | | | |
|---|---|---|---|
| 3,619,844 | 11/1971 | Collins et al. ...................... | 15/104.061 |
| 3,675,263 | 7/1972 | Durham ................................... | 15/211 |
| 3,939,519 | 2/1976 | Muirhead ........................... | 15/104.061 |
| 4,700,423 | 10/1987 | Zuliani .................................. | 15/236.05 |
| 4,798,246 | 1/1989 | Best ........................................ | 166/311 |
| 4,813,097 | 3/1989 | Simpson ................................ | 15/104.6 |
| 4,889,106 | 12/1989 | Watanabe ............................... | 15/104.2 |
| 5,437,073 | 8/1995 | Smith .................................. | 15/104.061 |
| 5,615,439 | 4/1997 | Bourrelly ............................... | 15/104.2 |

FOREIGN PATENT DOCUMENTS

| | | | |
|---|---|---|---|
| 0 123 762 | 11/1984 | European Pat. Off. . | |
| 0456402 | 11/1991 | European Pat. Off. .............. | 15/104.2 |

*Primary Examiner*—Mark Spisich
*Assistant Examiner*—Theresa T. Snider
*Attorney, Agent, or Firm*—Bruce F. Jacobs

[57] ABSTRACT

The invention relates to tube cleaners for hygienic cleaning of tubes, e.g. endoscopic tubes. A first embodiment has a body made of resilient material extending axially and having a socket at one end for mounting of the cleaner to the end of the rod. Integral blades project out from the body, each blade having an arcuate outer edge to scrape along the inside wall of the tube. The blades are at axially spaced locations and, in end view, they overlap so that cleaning occurs around 360°. A second embodiment has a core such as a wire, and the body and integral blades are moulded onto the wire core.

10 Claims, 3 Drawing Sheets

DEVICE FOR CLEANING MEDICAL ENDOSCOPIC TUBES

FIELD OF THE INVENTION

This invention relates to tube cleaners for internal cleaning of tubes for hygienic purposes, particularly for endoscopic tubes used for medical and veterinary procedures. However the tube cleaner may also suitable for use in internal cleaning of tubes in other fields requiring hygiene, such as in cleaning of tubes used in the food and beverage industries, and in the pharmaceutical, natural or herbal substance industries.

BACKGROUND OF THE INVENTION

Stainless steel or other material tubes are used in endoscopic surgery or procedures by insertion of the tubes into a patient's body, such as into body cavities, canals or passages in the body, or transdermally into body cavities, tissues or organs. Instruments are inserted through such tubes, e.g. for observation or inspection, for carrying out medical procedures at the open end of the tube inserted into the patient's body, and/or for insertion, location and placement of articles into the patient's body. Obviously such tubes must be thoroughly cleaned and sterilised before re-use. There are no particular problems with external cleaning of the tubes but internal cleaning is presently carried out using simple bristle tube cleaners. These bristle cleaners each comprise essentially a wire central body which is inserted into the tube, the wire having flexible bristles projecting radially along part of the length of the wire body so that the person cleaning the tool simply scrubs back and forth while periodically flushing the tube with a sanitising or sterilising solvent or solution. The bristles each contact the internal walls with effectively a point contact so that prolonged scrubbing is necessary to ensure reasonable probability that all surfaces have been effectively cleaned. However time pressure on the person cleaning the tube can induce shortening of the scrubbing time. Also, even prolonged scrubbing still leaves some statistical risk that parts of the internal surface have not been contacted by the bristles.

A tube cleaner for hygienic internal cleaning of tubes may also find application in other areas such as in cleaning of tubes used for conveying food and beverage products, pharmaceutical products or ingredients or carriers for pharmaceutical products, natural or herbal products or ingredients or carriers therefor, and possibly in the chemical industries.

OBJECTS OF THE INVENTION

It is an object of the present invention to provide a tube cleaner which can be used for effective internal cleaning of tubes, particularly for hygienic purposes.

It is a preferred object of the present invention to provide an endoscopic tube cleaner suitable for effective cleaning of endoscopic tubes used in medical and veterinary procedures.

A further preferred object is to provide a tube cleaner suitable for effective internal cleaning of tubes having small internal diameters, e.g. in the order of 2.5 mm.

SUMMARY OF THE INVENTION

According to the present invention there is provided a tube cleaner for internal cleaning of a tube for hygienic purposes, the tube cleaner having a body which extends axially in relation to the tube and a plurality of blades integral with the body and projecting out from the body at axially spaced locations, each blade having an outer edge and a sufficient radial dimension so that the outer edge engages the walls of the tube in an arc of the tube in cross section so that the blades scrape along the tube walls as the body moves along the tube, the blades being composed of a resilient material so as to remain in scraping contact with the walls as the body moves along the tube.

Preferably numbers of the blades are provided at axially spaced positions lengthwise on the body and are rotationally staggered in their angular placement around the axis of the body so that the blades will scrape along the walls of the tube throughout 360° relative to the axis of the tube as the tube cleaner moves along the tube.

In one possible embodiment, the outer edge of each blade is arcuate in end view and subtends an angle at the axis of the body of less than 180°. For example, the outer edge of each blade may subtend an angle at the axis of the body of less than 90°, there being multiple blades provided around the body at each of a member of axially spaced blade locations, and there are generally sector shaped gaps left between the outer edges of circumferentially adjacent blades at each of the axially spaced blade locations, the gaps enabling matter dislodged from the tube to move between circumferentially adjacent blades at each of the axially spaced blade locations.

At least one of the blades may have a side edge extending inwardly from the outer edge to the body in a non-radial direction so that the point of intersection of the side edge with the outer edge defines an acute angled corner whereby movement of the tube cleaner in the tube with a component of rotary motion enables the acute angled corner to provide a circumferential scraping action to help dislodge particulate material adhering inside the tube.

In a first embodiment of the invention the body has a formation at an axial end thereof for mounting of the body to a support member by which the tube cleaner can be mounted and pushed and pulled back and forth in the tube. Where the body is composed of a flexible and resilient material, the body may be provided with an axially extending socket for receiving the support member therein so that the resilience of the material from which the body is composed enables the body to grip the support member and retain the tube cleaner mounted on the support member. The first embodiment provides a tube cleaner in combination with a support member, the support member having a deformation thereon which is received within the socket in the body and which provides a tight interference fit for secure mounting of the body to the support member. The deformation may comprise a nip or pinch formed in the outside surface of the support member so as to provide a projecting portion which distorts the internal wall of the socket in the body so that, because of the resilience of the material of which the tube cleaner is composed, the distorted or deformed internal wall of the socket will tightly engage with the projecting portion of the support member.

The first embodiment of the tube cleaner which is provided with a socket in the body so as to be mounted on the end of a support member such as a rod is difficult or impractical to be manufactured and/or used for very small tubes. Some tubes used for endoscopic purposes can have a central bore as small as 2.5 mm in diameter. For such small diameter tubes, the same principal features of the invention can be used, namely the body extending axially, a number of integral blades projecting from the body at axially spaced locations, and each blade having an outer edge to engage the walls of the tube in an arc so that the blades scrape along the tube walls, the blades being composed of a resilient material. However, for small diameter tubes (and also if desired for larger diameter tubes), the body which extends axially is preferably provided with blades projecting therefrom, each blade having an outer edge which is arcuate in end view and which subtends an angle of at least 180° at the axis of the body, there being one blade provided at each of a number of axially spaced blade locations. For example, the outer edge of each blade may subtend an angle of about 200° at the axis. Preferably the centre point of the arcuate outer edge of each blade is angularly shifted 180° around the axis from the centre point of the outer edge of the next axially adjacent blade so that there are blades of alternating position along the axial direction, the blades being spaced axially so that in end view the blades overlap and thereby will scrap along the walls of the tube throughout 360° in relation to the axis of the tube as the tube cleaner moves along the tube.

Preferably the body of the tube cleaner particularly adapted for small tubes comprises a structural axially extending core and a sheath of flexible material around the core. For example, the core may comprise a wire, such as a stainless steel wire, and the sheath may be made of the same flexible material as the blades and be moulded around the core integral with the blades. The parting line of the opposed mould parts may define a diameter of each blade, the diameter extending, in the case of a blade subtending 200° at the axis, from a first end point on the arcuate outer edge angularly spaced 10° from a diameter through the axis of the tube cleaner to a second end point angularly spaced 10° past the other end of the diameter. Thus, with this arrangement, one mould part will have a semi-circular disc shaped cavity for moulding the major part of a blade and the facing mould part will have two relatively shallow cavities forming the last sectors of the blades subtending 10° at the axis of the body.

The present invention also provides an endoscopic tube cleaner for cleaning of endoscopic tubes for medical or veterinary purposes, the endoscopic tube cleaner having the constructional and functional features of the tube cleaner described above for generalised hygienic tube cleaning purposes.

DESCRIPTION OF THE DRAWINGS

Possible and preferred features of the present invention will now be described with particular reference to the accompanying drawings. However it is to be understood that the features illustrated in and described with reference to the drawings are not to be construed as limiting on the scope of the invention. In the drawings.

DESCRIPTION OF THE PREFERRED EMBODIMENTS

Figure 1:
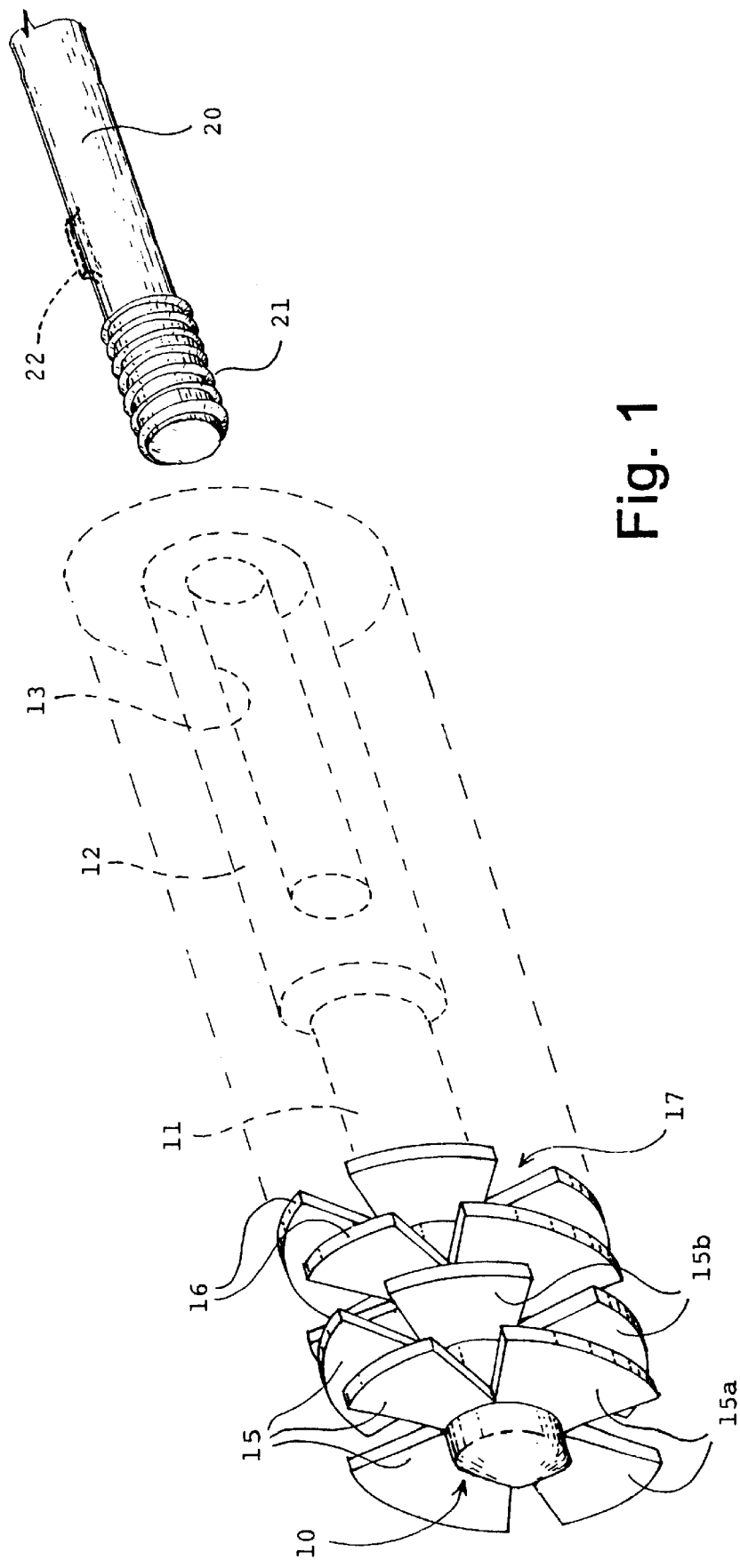
FIG. 1 is a perspective view of a tube cleaner according to a preferred first embodiment of the present invention.
Figure 2:
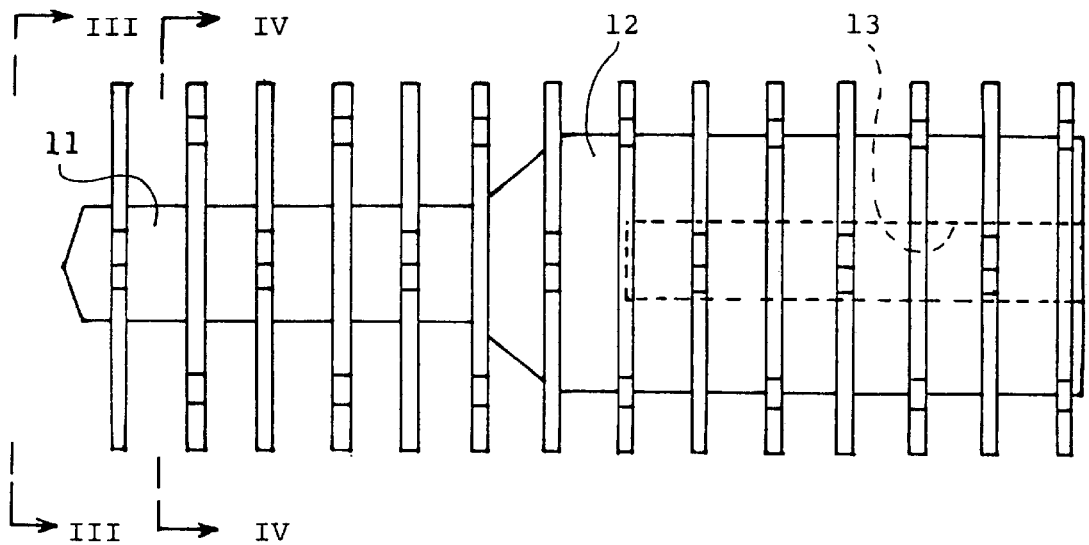
FIG. 2 is a side view of the tube cleaner shown in FIG. 1.

The tube cleaner in FIGS. 1 to 4 of the drawings has a central axially extending body 10. The body has a cylindrical front end 11 extending along approximately half the length of the body and a larger diameter back end 12 providing a mounting for the tube cleaner. In particular, the back end 12 has a formation shown as an axial socket 13 into which a support rod 20, or other support member, can be inserted to mount the tube cleaner at the end of the rod. For example, the end 21 of the support rod 20 may be provided with a self tapping thread so as to be screwed into the axial socket 13 and hold the tube cleaner securely at the end of the rod. The axial socket 13 is not illustrated as having an internal thread, since this is not necessary given the material from which the tube cleaner is made as described below. The soft but resilient material enables the self tapping threaded end 21 of the support rod 20 to be screwed into the axial socket 13 causing the walls of the socket 13 to deform to accept the thread and securely mount the tube cleaner at the end of the rod 20 which can be pushed back and forth in the tube being cleaned without the tube cleaner detaching from the end of the support rod. It will be appreciated that the tube cleaner does not need to be mounted at the end of a support rod but instead can be mounted for example at the end of a flexible line by which the tube cleaner can be moved through the tube, particularly if cleaning around curved tubes is needed. In a further possibility, the tube cleaner may be arranged to be forced through the tube by fluid pressure applied behind the cleaner.

Projecting from the body 10 are blades 15 which are provided at axially spaced locations along the body. Each blade has an outer edge 16 to engage the walls of the tube around an arc of the tube in cross section so that each blade scrapes along the walls. As seen best in FIGS. 3 and 4, each outer edge 16 in end view is arcuate and subtends an angle at the axis of the body of less than 180°. In the illustrated embodiment where there are four blades provided around the body at each axial blade location, each outer edge 16 subtends an angle at the axis of the body of less than 90°, thereby leaving generally sector shaped gaps 17 between circumferentially adjacent blades. The gaps 17 enable dislodged matter from the tube to pass between circumferentially adjacent blades and to pass along the tube cleaner between consecutive axially spaced blade locations reducing the likelihood of clogging of the tube cleaner and impairment of the scraping action along the walls.

The axially adjacent but spaced blades are rotationally staggered in their angular placement around the axis of the body 10. In the illustrated embodiment, the blades 15a in the first axial blade position are rotationally staggered relative to the blades 15b in the second axial blade position so that, when the cleaner is viewed in the axial direction, the gaps 17a between the blades 15a are completely covered by the immediately trailing blades 15b in the ring of blades at the second axial blade position. With this arrangement, the blades 15a, 15b will scrape along the walls of the tube throughout 360° around the axis of the tube as the tube cleaner is moved along the tube. As seen in FIG. 1, the odd numbered positions of the axially spaced rings of blades can have their blades in the same angular positions, as can the blades in the even numbered positions of the axially spaced rings of blades. However clearly this is not essential.

Figure 3:
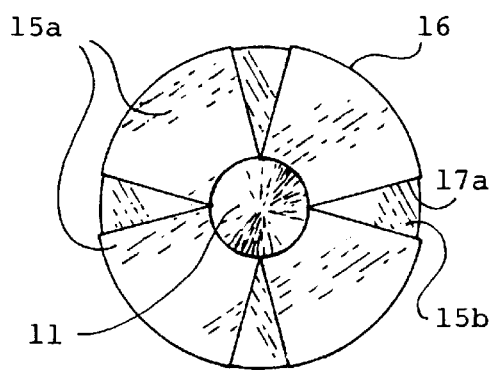
FIG. 3 is a cross sectional view looking at the first ring of blades and taken along the line III—III in FIG. 2.
Figure 4:
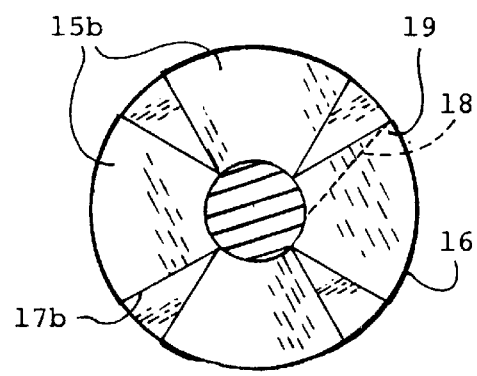
FIG. 4 is a cross sectional view looking at the second ring of blades and taken along the line IV—IV in FIG. 2.

The corners of the outer edges 16 where the gaps 17 are provided may be defined by generally radial lines as shown in FIGS. 3 and 4. However if desired, one side edge 18 of one or more blades as shown in FIG. 4 may be non-radial or may extend in a chordal direction so that the point of intersection of the edge 18 with the outer edge 16 defines an acute angled corner 19. With a component of rotary movement of the tube cleaner as it is moved in the tube, such corners 19 can have a circumferential scraping action to help dislodge particulate material adhering inside the tube.

The entire tube cleaner is preferably of integral construction and therefore is preferably made by a moulding process. The material from which the tube cleaner is made may be any suitable resilient material such as a rubber or synthetic plastics material. The use of a flexible and resilient material enables the tube cleaner to be readily inserted into the tube which will have an internal diameter slightly smaller than the diameter defined by the outer edges 16 of the blades 15. The resilience of the material will maintain the outer edges 16 in contact with the inner walls of the tube as the tube cleaner is pushed and pulled back and forth in the tube. The tube cleaners can be manufactured cheaply so that they can be discarded after use.

Figure 5:
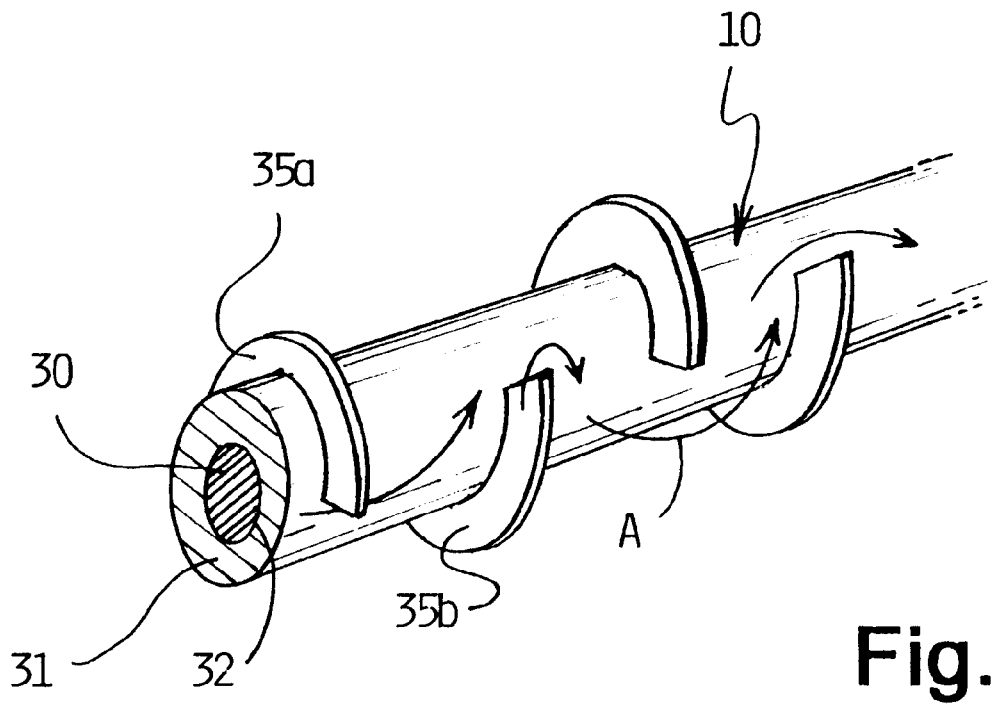
FIG. 5 is a perspective view of a different tube cleaner suitable for small diameter tubes and according to a preferred second embodiment of the present invention.
Figure 6:
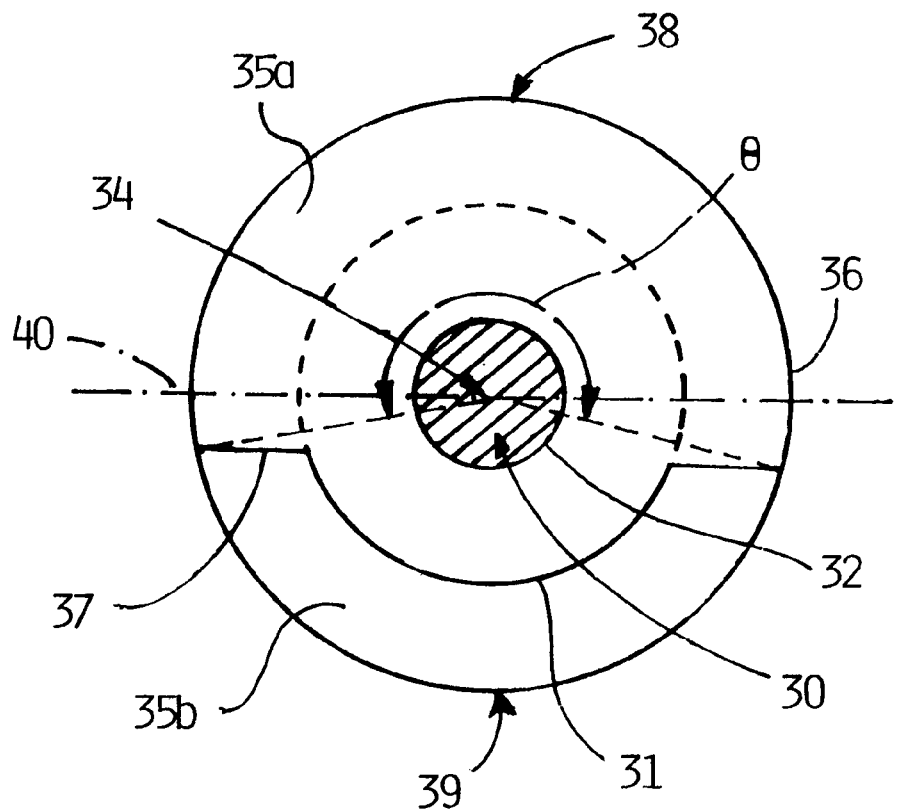
FIG. 6 is a section through the tube clearer of FIG. 5.

The tube cleaner illustrated in FIGS. 5 and 6 has a central axially extending body 10 having a structural axial core 30, e.g. composed of a stainless steel wire 32. Surrounding the core 30 is a cylindrical sheath 31. The core 30 can extend for any desired distance or length beyond one end of the body 10 so as to form a handle by which the tube cleaner can be inserted into a tube and pushed and pulled back and forth to clean the inside of the tube. The sheath 31 is an intimate or tight interference fit with the core 30 and preferably this is achieved by moulding the sheath 31 around the wire 32 forming the core 30.

Projecting from the body 10 are blades 35*a*, 35*b* which are provided at axially spaced locations along the body. Each blade has an outer edge 36 to engage the walls of the tube around an arc of the tube cross section so that each blade scrapes along the walls. As shown in FIG. 6, each outer edge 36 in end view is arcuate and subtends an angle θ at the axis 34 of the body of greater than 180°. In the particular illustrated embodiment, the axially adjacent but spaced blades 35*a*, 35*b* are rotationally staggered in their angular placement around the axis of the body 10. In particular, the centre point 38 of the outer edge 36 of blade 35*a* is angularly shifted 180° around to the axis 34 from the centre point 39 of the outer edge of the next axially adjacent blade 35*b*. Because each blade 35*a*, 35*b* subtends an angle of greater than 180°, the blade edges 36 in end view extend around 360° so that the outer edges 36 will scrape along the surfaces of the bore in the tube throughout the entire circumference thereby cleaning the entire internal surface area of the tube as the tube cleaner is pushed and pulled back and forth in the tube. The gaps left between the side edges 37 of the blades and the internal surface of the tube (subtending about 160° in the illustrated embodiment) enable dislodged matter from the tube walls to move between consecutive axially spaced blades as shown in FIG. 5 by the arrows A, particularly if cleaning liquid is provided to flow in the tube simultaneously with the wiping and scrubbing action of the tube cleaner, thereby reducing the likelihood of clogging of the tube cleaner and impairment of the scraping action along the tube walls.

The blades 35*a*, 35*b* and the sheath 31 are moulded integrally around the wire 32 defining the core 30. By providing two mould parts which separate along the diametrical line 40, at the position of each blade, one mould part will have a semi-circular mould cavity in which 180° of a blade is formed, the remaining 20° of the blade being formed in two 10° cavities provided in the opposite mould part. The wire 32 forming the core 30 will be located extending axially through the mould cavity when the two mould parts are brought together preparatory to injection of the material.

The material from which the sheath 31 and blades 35*a*, 35*b* are formed may be any suitable resilient material such as a rubber or synthetic plastics material. The use of a flexible and resilient material enables the tube cleaner to be readily inserted into the tube which may have an internal diameter slightly smaller than the diameter defined by the outer edges 36 of the blades 35*a*, 35*b*. The resilience of the material will maintain the outer edges 36 in contact with the inner walls of the tube as the tube cleaner is pushed and pulled back and forth in the tube. The tube cleaners can be sterilised after use although they can be manufactured cheaply so that they can be discarded after use.

An example of a tube cleaner suitable for cleaning a tube having an internal diameter of 2.5 mm can have a wire 32 defining the structural core 30 having a diameter of 0.5 mm, the diameter of the sheath 31 can be 1.5 mm (i.e. the thickness of the material forming the sheath around the core 30 is 0.5 mm), and the outer edges 36 of the blades can have a diameter of 2.5 mm (i.e. the blades extend 0.5 mm beyond the outside surface of the sheath 31). The length of the body may be for example about 40 mm although, as mentioned earlier, the wire forming the core 30 can extend for any length desired beyond the body to enable the tube cleaner to be held and worked back and forth in the tube being cleaned. The number of blades along the 40 mm length of the body may be in the range 10 to 35. It will be understood that in the tube cleaner illustrated in FIG. 5, the spacing between axially adjacent blades may be exaggerated for clarity, i.e. the spacing is shown significantly greater than the actual spacing.

The tube cleaners described and illustrated herein can effectively clean tubes internally, particularly endoscopic tubes for medical and veterinary uses with the outer edges of the blades reaching all internal surfaces particularly compared to bristle tube cleaners. The construction in FIGS. 5 and 6 is particularly suitable for use with small diameter tubes, e.g. endoscopic tubes of 2.5 mm internal diameter.

It will be appreciated that modifications and alterations can be made to the described illustrated embodiments without departing from the invention. For example, the blades are illustrated as being planar blades with the planes of the blades being at right angles to the axial direction. However clearly the blades could be in planes at the same or differing angles to the axial direction, including both positive and negative angles within the one tube cleaner.

The particular embodiment of the tube cleaner in FIGS. 1 to 4 has a central axial socket 13 opening at one end of the body and into which the end of the rod 20 is inserted to mount the tube cleaner on the end of the rod. In these figures, the end 21 of the rod is threaded so that the end of the rod can be screwed into the socket with the resilient material from which the body of the tube cleaner is made enabling the walls of the socket to yield to receive the thread. However, the provision of a thread on the end of the mounting rod can add significantly to the manufacturing cost of the rod. It has been found, or it is proposed, that there is no need for the end of the rod to be threaded provided that there is a formation which promotes a tight interference fit for secure mounting of the tube cleaner to the end of the rod. It is proposed, for example, that a deformation provided in the outside surface of the rod adjacent the end, such as a nip or pinch 22 (FIG. 1) formed in the outside surface of the rod will form a projecting portion which will distort the internal wall of the socket and, because of the resilience of the material from which the tube cleaner is formed, the distorted or deformed socket walls will tightly engage with the rod particularly at the projecting portion formed by the nip or pinch 22. This will be sufficient to securely hold the tube cleaner on the end of the rod without the need for machining a thread on the end of the rod.

A further modification or improvement of the tube cleaner in FIGS. 1 to 4 relates to the formation of the body extending axially. Instead of the body having a larger diameter back end 12 in which the axial mounting socket 13 is provided and a narrower diameter solid cylindrical front end 11, the body may have the cylindrical socket extending along most or substantially all the entire length of the body. For example, with the tube cleaner having a length of about 25 mm, the axial mounting socket may be provided along substantially the entire length except for a short piece at one end where the socket is closed (opposite to the end provided with the mouth into which the mounting rod is inserted). Providing a relatively long mounting socket, compared to the embodiment illustrated in FIGS. 1 to 4, enables a more secure mounting of the tube cleaner to the end of the rod to be provided since the tube cleaner can grip the end of the rod along substantially the entire length of the socket.

In a further modification or improvement enabling the tube cleaner to be discarded after use but the rod to be reused by placing a new tube cleaner on the end, the used tube cleaner can be ejected from the end without need for touching the tube cleaner after use. This can be achieved by providing an ejector rod extending axially through the mounting rod, the ejector rod having a head at the end of the rod, the other end of the ejector rod remote from the end where the tube cleaner is mounted having some means by which the ejector rod can be moved telescopically within the mounting rod. With this arrangement, the head of the ejector rod can be retracted back against the end of the mounting rod when the tube cleaner is mounted thereon. After use, the ejector rod can be telescopically advanced so that the head will push the tube cleaner off the end of the rod. The rod can be sterilised readily before a new tube cleaner is mounted thereon for a subsequent tube cleaning operation.

The particular illustrated embodiments have axially spaced rings or groups of blades throughout the entire length so that there are paths for fluid flow and for flow or movement of matter through the gaps 17 from one end of the tube cleaner to the other. However if desired one or more uninterrupted rings, lips or annuli may be provided extending around the body throughout 360°. This may be useful if the tube cleaner is to be forced through a tube by fluid pressure applied behind the tube cleaner. However the provision of one or more uninterrupted circumferential lips or rings is not preferred for cleaning of endoscopic tubes by a back and forth scrubbing action since dislodged matter is more likely to accumulate at such uninterrupted rings thereby possibly impairing flushing of dislodged material from the tubes if the scrubbing of the tubes while immersed is the procedure of the person cleaning the tubes.

It is to be understood that various alterations, modifications and/or additions may be made to the features of the possible and preferred embodiment(s) of the invention as defined in the following claims without departing from the scope of the invention.

What I claim is:

1. An endoscopic tube cleaner for internal cleaning of an endoscopic tube for medical procedures, the tube cleaner having a body which extends axially in relation to the tube and a plurality of blades integral with the body and projecting out from the body at axially spaced locations, each blade having an outer edge and a sufficient radial dimension so that the outer edge engages the walls of the endoscopic tube in an arc of less than 360° of the tube in cross section so that each of the blades wipes along the tube walls as the body moves along the tube but leaves at least one gap in the area of the walls contacted and wiped by the blade, the blades being composed of a flexible resilient material capable of sterilization so as to remain in wiping contact with the walls as the body moves along the tube, the tube cleaner including at least one of said blades provided at each of first and subsequent axially spaced locations lengthwise on the body and which are rotationally staggered in their angular placement around the axis of the body so that when the tube cleaner is viewed in the axial direction, the at least one gap in the area of the walls not contacted and wiped by said at least one of said blades at the first location is completely covered by the immediately adjacent said at least one of said blades at the next subsequent axially spaced location and wherein the at least one gap allows for dislodged matter to move between consecutive axially spaced blades, whereby the blades at the first and next subsequent axially spaced location wipe along the walls of the tube throughout 360° relative to the axis of the tube as the tube cleaner moves along the tube.

2. An endoscopic tube cleaner as claimed in claim 1 wherein the outer edge of each blade is arcuate in end view and subtends an angle at the axis of the body of less than 180°.

3. An endoscopic tube cleaner as claimed in claim 2 wherein the outer edge of each blade subtends an angle at the axis of the body of less than 90°, there being multiple blades provided around the body at each of the first and subsequent axially spaced blade locations, and each said at least one gap is a generally sector shaped gap left between the outer edges of circumferentially adjacent blades at each of the axially spaced blade locations, the gaps enabling matter dislodged from the tube to move between circumferentially adjacent blades at each of the axially spaced blade locations.

4. An endoscopic tube cleaner as claimed in claim 3, wherein the multiple blades provided at the location immediately adjacent and next subsequent to the multiple blades at the first location are rotationally staggered at 45° in their angular placement around the axis of the body relative to the angular placements of the multiple blades at the first location.

5. An endoscopic tube cleaner as claimed in claim 1 wherein the body comprises a structural axially extending core and a sheath of flexible material around the core and from which the integral blades project, the core comprising a wire and the sheath and blades being moulded around the wire.

6. An endoscopic tube cleaner for internal cleaning of an endoscopic tube for medical procedures, the tube cleaner having a body which extends axially in relation to the tube and a plurality of blades integral with the body and projecting out from the body at axially spaced locations, each blade having an outer edge and a sufficient radial dimension so that the outer edge engages the walls of the tube in an arc, the outer edge of each blade being arcuate in end view and subtending an angle at the axis of the body of at least 180°, whereby each of the blades wipes along the tube walls as the body moves along the tube but leaves at least one gap in the area of the walls contacted and wiped by the blade, the blades being composed of a flexible resilient material capable of sterilization so as to remain in wiping contact with the walls as the body moves along the tube, there being one blade provided at each of a number of axially spaced blade locations including one blade at each of first and second axially spaced locations lengthwise on the body, the blades at the first and second axially spaced locations being rotationally staggered in their angular placement round the axis of the body so that when the tube cleaner is viewed in the axial direction, the gap in the area of the walls not contacted and wiped by said one blade at the first location is completely covered by the immediately adjacent said one blade at the second axially spaced location and wherein the at least one gap allows for dislodged matter to move between consecutive axially spaced blades, whereby the blades at the first and second axially spaced locations will wipe along the walls of the tube throughout 360° relative to the axis of the tube as the tube cleaner moves along the tube.

7. An endoscopic tube cleaner as claimed in claim 6 wherein each blade has a centre point of its arcuate outer edge, the centre point of the outer edge of each blade being angularly shifted 180° around the longitudinal axis of the body from the centre point of the outer edge of the next axially adjacent blade so that there are blades of alternating positions along the axial direction.

8. A tube cleaner for internal cleaning of a tube for hygienic purposes, the tube cleaner having a body which extends axially in relation to the tube and a plurality of blades integral with the body and protecting out from the body at axially spaced locations, each blade having an outer edge and a sufficient radial dimension so that the outer edge engages the walls of the tube in an arc of the tube in cross section so that the blades wipe along the tube walls as the body moves along the tube, the blades being composed of a resilient material so as to remain in wiping contact with the walls as the body moves along the tube, the body being provided with a formation at an axial end thereof for mounting of the body to a support member by which the tube cleaner can be mounted and can be pushed and pulled back and forth in the tube, the body being composed of a flexible and resilient material, the formation at the axial end of the body comprising an axially extending socket for receiving the support member therein so that the resilience of the material from which the body is composed enables the body to grip the support member and retain the tube cleaner mounted on the support member.

9. A tube cleaner as claimed in claim 8 in combination with a support member, the support member having a deformation thereon which is received within the socket in the body and which provides a tight interference fit for secure mounting of the body to the support member.

10. A tube cleaner in combination with a support member as claimed in claim 9 wherein the deformation comprises a nip or pinch formed in the outside surface of the support member so as to provide a projecting portion which distorts the internal wall of the socket in the body so that, because of the resilience of the material of which the tube cleaner is composed, the distorted or deformed internal wall of the socket will tightly engage with the projecting portion of the support member.

* * * * *